United States Patent
Kim et al.

(10) Patent No.: US 12,380,629 B2
(45) Date of Patent: Aug. 5, 2025

(54) AUTOMATED REGISTRATION METHOD OF 3D FACIAL SCAN DATA AND 3D VOLUMETRIC MEDICAL IMAGE DATA USING DEEP LEARNING AND COMPUTER READABLE MEDIUM HAVING PROGRAM FOR PERFORMING THE METHOD

(71) Applicant: IMAGOWORKS INC., Seoul (KR)

(72) Inventors: Hannah Kim, Seoul (KR); Bonjour Shin, Seoul (KR); Jinhyeok Choi, Seoul (KR); Youngjun Kim, Seoul (KR)

(73) Assignee: IMAGOWORKS INC., Seoul (KR)

(*) Notice: Subject to any disclaimer, the term of this patent is extended or adjusted under 35 U.S.C. 154(b) by 215 days.

(21) Appl. No.: 18/111,709

(22) Filed: Feb. 20, 2023

(65) Prior Publication Data
US 2023/0306677 A1    Sep. 28, 2023

(30) Foreign Application Priority Data
Feb. 28, 2022 (KR) .................. 10-2022-0026434

(51) Int. Cl.
*G06T 15/08* (2011.01)
*G06T 7/50* (2017.01)
(Continued)

(52) U.S. Cl.
CPC .............. *G06T 15/08* (2013.01); *G06T 7/50* (2017.01); *G06V 10/60* (2022.01); *G06V 10/761* (2022.01);
(Continued)

(58) Field of Classification Search
CPC . G06T 15/08; G06T 7/50; G06T 2207/10028; G06T 2207/10081;
(Continued)

(56) References Cited

U.S. PATENT DOCUMENTS

2005/0063582 A1* 3/2005 Park .................. G06T 17/10
382/181
2005/0243323 A1* 11/2005 Hsu ..................... G06T 7/30
356/450
(Continued)

FOREIGN PATENT DOCUMENTS

KR    20190101694 A    9/2019
KR    102273437 B1     7/2021
(Continued)

OTHER PUBLICATIONS

Automatic Registration Between Dental Cone-Beam CT and Scanned Surface via Deep Pose Regression Neural Networks and Clustered Similarities, Chung et al., IEEE Transactions on Medical Imaging, (Year: 2020).*
(Continued)

*Primary Examiner* — Michael Le
(74) *Attorney, Agent, or Firm* — LEEPI

(57) ABSTRACT

An automated registration method of 3D facial scan data and 3D volumetric medical image data using deep learning, includes extracting scan landmarks from the 3D facial scan data using a convolutional neural network, extracting volume landmarks from the 3D volumetric medical image data using the convolutional neural network and operating an initial registration of the 3D facial scan data and the 3D volumetric medical image data using the scan landmarks and the volume landmarks.

25 Claims, 15 Drawing Sheets

(51) Int. Cl.
  *G06V 10/60* (2022.01)
  *G06V 10/74* (2022.01)
  *G06V 40/16* (2022.01)

(52) U.S. Cl.
  CPC .. *G06V 40/171* (2022.01); *G06T 2207/10028* (2013.01); *G06T 2207/10081* (2013.01); *G06T 2207/10088* (2013.01); *G06T 2207/10104* (2013.01); *G06T 2207/20084* (2013.01); *G06T 2207/30201* (2013.01)

(58) Field of Classification Search
  CPC . G06T 2207/10088; G06T 2207/10104; G06T 2207/20084; G06T 2207/30201; G06T 7/33; G06T 7/11; G06V 10/60; G06V 10/761; G06V 40/171; G06V 10/82; G06V 20/647; G06V 20/653; G06N 3/04; G16H 30/40
  See application file for complete search history.

(56) References Cited

U.S. PATENT DOCUMENTS

| | | | | |
|---|---|---|---|---|
| 2020/0035351 | A1* | 1/2020 | Kim | G16H 50/30 |
| 2021/0085294 | A1* | 3/2021 | Salles | A61B 8/466 |
| 2021/0358212 | A1* | 11/2021 | Vesdapunt | G06V 40/166 |
| 2022/0215625 | A1* | 7/2022 | Xia | A61B 6/501 |
| 2022/0358692 | A1* | 11/2022 | Bhushan | A61B 5/055 |
| 2022/0395329 | A1* | 12/2022 | Seo | A61F 2/12 |
| 2024/0095876 | A1* | 3/2024 | Bagherinia | G06T 3/14 |

FOREIGN PATENT DOCUMENTS

| | | |
|---|---|---|
| KR | 102273438 B1 | 7/2021 |
| KR | 20210088946 A | 7/2021 |
| WO | 2020206135 A1 | 10/2020 |
| WO | 2021125851 A1 | 6/2021 |

OTHER PUBLICATIONS

Three-dimensional soft tissue changes according to skeletal changes after mandibular setback surgery by using cone-beam computed tomography and a structured light scanner, Kyung-A Kim, et. al.,Progress in Orthodontics, 2019, pp. 20-25. (Year: 2019).*
Multi-view consensus CNN for 3D facial landmark placement, Rasmus R. Paulsen, et. al. (Year: 2018).*
Jeongjin Lee, Accurate Registration Method of 3D Facial Scan Data and CBCT Data using Distance Map, Journal of Korea Multimedia Society, Oct. 2015, pp. 1157-1163, vol. 18. No. 10, Korea.
Extended European search report dated on Jul. 13, 2023.
Three-dimensional soft tissue changes according to skeletal changes after mandibular setback surgery by using cone beam computed tomography and a structured light scanner, Kyung-A Kim, et al., Progress in Orthodontics, 2019, pp. 20-25.
Multi-view consensus CNN for 3D facial landmark placement, Rasmus R. Paulsen, et al.

* cited by examiner

Initial Registration

Fine Registration

AUTOMATED REGISTRATION METHOD OF 3D FACIAL SCAN DATA AND 3D VOLUMETRIC MEDICAL IMAGE DATA USING DEEP LEARNING AND COMPUTER READABLE MEDIUM HAVING PROGRAM FOR PERFORMING THE METHOD

PRIORITY STATEMENT

This application claims priority under 35 U.S.C. § 119 to Korean Patent Application No. 10-2022-0026434, filed on Feb. 28, 2022 in the Korean Intellectual Property Office (KIPO) and International Patent Application No. PCT/KR2022/003132 filed on Mar. 4, 2022, the contents of which are herein incorporated by reference in their entireties.

BACKGROUND

1. Technical Field

Embodiments relate to an automated registration method of three dimensional (3D) facial scan data and 3D volumetric medical image data using deep learning and a non-transitory computer-readable storage medium having stored thereon program instructions of the automated registration method of 3D facial scan data and 3D volumetric medical image data. More particularly, embodiments relate to an automated registration method of 3D facial scan data and 3D volumetric medical image data using deep learning and not requiring a user input or a conversion of a data structure and a non-transitory computer-readable storage medium having stored thereon program instructions of the automated registration method of 3D facial scan data and 3D volumetric medical image data.

2. Description of the Related Art

A 3D volumetric medical image data may refer to accumulated data of hundreds of two dimensional (2D) slide images such as computed tomography (CT) images, cone-beam CT (CBCT) images and magnetic resonance imaging (MRI) images. The 3D volumetric medical image data may include various tissues and structures of a body in a 3D form so that the 3D volumetric medical image data may be widely used for diagnosis, treatment and surgical planning in most medical fields including internal medicine and surgery. In dentistry, oral and maxillofacial surgery and plastic surgery, etc., the 3D volumetric medical image data for a head and neck region may be acquired and used to diagnose and treat a patient's maxillofacial and oral cavity.

The head and neck region may be an important body region because of aesthetic aspects as well as functional aspects such as breathing, mastication, and pronunciation. Therefore, both functional considerations and aesthetic preferences of a patient are reflected in maxillofacial and oral procedures and surgical plans. However, the 3D volumetric medical image data has intensity information of only a single channel and does not include information about colors of various tissues and structures of the body.

In addition, in order to three-dimensionally analyze a shape of a specific area, a process of segmenting the area or reconstructing the segmented data into a 3D model may be required. The process of segmenting the area and reconstructing the segmented data may require a lot of time. In addition, the 3D volumetric medical image data is expensive to acquire, and in the case of CT or CBCT, it is difficult to acquire multiple times due to the risk of radiation exposure. Therefore, it is difficult to compare the 3D volumetric medical image data before surgery and the 3D volumetric medical image data after surgery and it is difficult to use the 3D volumetric medical image data for procedures and surgical simulations in various facial expression states.

In order to compensate for these limitations of 3D volumetric medical image data, 3D facial scan mesh model data are being used with the 3D volumetric medical image data. The 3D volumetric medical image data may include texture, which is color information, as well as 3D shape information of the face shape and is inexpensive to acquire. A patient may not be exposed to radiation at all during the acquisition process of the 3D volumetric medical image data. Therefore, it is easy to compare the 3D volumetric medical image data before surgery and the 3D volumetric medical image data after surgery and it is easy to use the 3D volumetric medical image data for procedures and surgical simulations in various facial expression states.

In addition, when the 3D facial scan mesh model data are used with the 3D volumetric medical image data, it is helpful in establishing a procedure and surgical plan considering the aesthetic shape and color as well as the anatomical information of the inside of the head and neck region. However, since the 3D volumetric medical image data and the 3D facial scan mesh model data have different 3D spatial coordinate systems, a registration process of aligning and overlapping these two data must be preceded. However, a manual registration process in the 3D space requires skill and a lot of time.

Conventionally, methods for registration of 3D facial scan mesh model data and 3D volumetric medical image data have been proposed for this purpose. Since the 3D facial scan mesh model data and the 3D volumetric medical image data have different data structures, a process of unifying the different data structures into one was preceded in the conventional methods. The conventional methods are divided into following two methods: 1. a method of performing a 3D mesh-based registration after unifying a skin area into 3D mesh model data by segmentation and 3D reconstruction of 3D volumetric medical image data; 2. a method of performing an image-based registration by voxelizing the 3D facial scan mesh data into the 3D volumetric medical image data. However, the above mentioned segmentation and 3D reconstruction are time consuming tasks. In addition, when the 3D volumetric medical image data have a low image quality like CBCT, or the data have a heavy metal noise due to dental prosthesis or braces, the segmentation may be difficult so that the above mentioned method may not be applied.

In the case of a method of voxelization of the 3D facial scan mesh data, the shape information of the mesh data may be lost so that an accuracy of the registration may be decreased.

Furthermore, in another conventional method, matching points may be manually inputted to two different data and the matching points of the two different data may be overlapped. In another conventional method, markers may be attached to the patient, two different data having the markers may be acquired and a marker-based registration of the two different data may be performed. In the method of using the manual matching points, it is difficult to input accurate matching points, so that inconsistent results may be derived depending on a user or the same user's repetitive work. In the method of attaching the markers to the patient, the data must be acquired with the multiple markers attached to the patient so that the patient may experience discomfort. In addition, in the method of attaching the markers to the patient, a separate process of extracting markers through a user input or inputting marker positions may be required.

SUMMARY

Embodiments provide a fast automated registration method of 3D facial scan data and 3D volumetric medical image data using deep learning, not requiring a user input, an additional 3D model extraction process or a conversion of a data structure such as a voxelization, and utilizing the 3D facial scan data and the 3D volumetric medical image data itself.

Embodiments provide a non-transitory computer-readable storage medium having stored thereon program instructions of the automated registration method of 3D facial scan data and 3D volumetric medical image data.

In an example automated registration method of 3D facial scan data and 3D volumetric medical image data using deep learning according to the present inventive concept, the method includes extracting scan landmarks from the 3D facial scan data using a convolutional neural network, extracting volume landmarks from the 3D volumetric medical image data using the convolutional neural network and operating an initial registration of the 3D facial scan data and the 3D volumetric medical image data using the scan landmarks and the volume landmarks.

In an embodiment, the extracting scan landmarks may include generating a first 2D depth image representing a distance between a first reference plane disposed outside the 3D facial scan data and a face surface in the 3D facial scan data.

In an embodiment, an input of the convolutional neural network may be the first 2D depth image. An output of the convolutional neural network may be first 2D coordinates corresponding to the scan landmarks.

In an embodiment, the extracting scan landmarks may further include inverse-projecting the first 2D coordinates to first 3D coordinates based on a transformation method used when generating the first 2D depth image.

In an embodiment, an input of the convolutional neural network may be the first 2D depth image. An output of the convolutional neural network may be first 3D coordinates corresponding to the scan landmarks.

In an embodiment, the extracting volume landmarks may include generating a second 2D depth image representing a distance between a second reference plane disposed outside the 3D volumetric medical image data and a face surface in the 3D volumetric medical image data.

In an embodiment, in the generating a second 2D depth image, while moving from a starting point of the 3D volumetric medical image data to an inside of the 3D volumetric medical image data, a position where a change in brightness value is greater than a threshold value firstly may be generated as a depth value of the second 2D depth image.

In an embodiment, in the generating a second 2D depth image, while moving from a starting point of the 3D volumetric medical image data to an inside of the 3D volumetric medical image data, a position where a change in brightness value is greater than a threshold value firstly and having a brightness value within a predetermined range of skin brightness values may be generated as a depth value of the second 2D depth image.

In an embodiment, an input of the convolutional neural network may be the second 2D depth image. An output of the convolutional neural network may be second 2D coordinates corresponding to the volume landmarks.

In an embodiment, the extracting volume landmarks may further include inverse-projecting the second 2D coordinates to second 3D coordinates based on a transformation method used when generating the second 2D depth image.

In an embodiment, an input of the convolutional neural network may be the second 2D depth image. An output of the convolutional neural network may be second 3D coordinates corresponding to the scan landmarks.

In an embodiment, the extracting scan landmarks may include generating a first 2D captured image by capturing the 3D facial scan data.

In an embodiment, an input of the convolutional neural network may be the first 2D captured image. An output of the convolutional neural network may be first 3D coordinates corresponding to the scan landmarks.

In an embodiment, the extracting volume landmarks may include generating a second 2D captured image by capturing the 3D volume medical image data.

In an embodiment, an input of the convolutional neural network may be the second 2D captured image. An output of the convolutional neural network may be second 3D coordinates corresponding to the volume landmarks.

In an embodiment, a number of the scan landmarks extracted in the extracting scan landmarks may be equal to or greater than three. A number of the volume landmarks extracted in the extracting volume landmarks may be equal to or greater than three. The three or more scan landmarks may correspond to the three or more volume landmarks.

In an embodiment, the scan landmarks extracted in the extracting scan landmarks and the volume landmarks extracted in the extracting volume landmarks may include Soft tissue nasion, Right Exocanthion and Left Exocanthion respectively.

In an embodiment, the scan landmarks extracted in the extracting scan landmarks and the volume landmarks extracted in the extracting volume landmarks may include at least three among Soft tissue gabella, Soft tissue nasion, Supratip, Pronasale, Columella, Subnasale, Soft tissue A-point, Upper lip anterior point, Stomiom Superious, Lower point of gap between maxillary central incisors, Upper point of gap between mandibular central incisors, Stomiom Inferious, Lower lip anterior point, Soft tissue B-point, Soft tissue pogonion, Soft tissue gnathion, Soft tissue menton, Trichion, Right Orbitale superius, Left Orbitale superius, Right Palpebrale superius, Right Palpebrale inferious, Right Exocanthion, Right Endocanthion, Left Palpebrale superius, Left Palpebrale inferious, Left Endocanthion, Left Exocanthion, Right Zygion, Left Zygion, Right Cheilion, Left Cheilion, Right Tragus, Left Tragus, Right Soft tissue gonion, Left Soft tissue gonion, Right Alare, Left Alare, Right Alar curvature and Left Alar curvature respectively.

In an embodiment, the 3D facial scan data may be mesh data including 3D vertexes and triangle or rectangles generated by connecting the 3D vertexes.

In an embodiment, the 3D volumetric medical image data may be a medical image in which a patient's anatomy is obtained as 3D volumetric image data. The 3D volumetric medical image data may be one of a computed tomography (CT) image, a cone-beam CT (CBCT) image, a magnetic resonance imaging (MRI) image and a positron emission tomography (PET) image.

In an embodiment, the automated registration method may further include operating a fine registration after the operating an initial registration. In the fine registration, a distance between a plurality of sampling points in the 3D facial scan data and a plurality of sampling points in the 3D volumetric medical scan data may be adjusted to be less than a threshold distance.

In an example automated registration method of 3D facial scan data and 3D volumetric medical image data using deep learning according to the present inventive concept, the method includes extracting scan landmarks from the 3D facial scan data using a first convolutional neural network, extracting volume landmarks from the 3D volumetric medical image data using a second convolutional neural network different from the first convolutional neural network and operating an initial registration of the 3D facial scan data and the 3D volumetric medical image data using the scan landmarks and the volume landmarks.

In an example automated registration method of 3D facial scan data and 3D volumetric medical image data using deep learning according to the present inventive concept, extracting first scan landmarks from first 3D facial scan data using a convolutional neural network, extracting second scan landmarks from second 3D facial scan data using the convolutional neural network, extracting volume landmarks from the 3D volumetric medical image data using the convolutional neural network, operating an initial registration of the first 3D facial scan data, the second 3D facial scan data and the 3D volumetric medical image data using the first scan landmarks, the second scan landmarks and the volume landmarks and calculating a surface distance between the first 3D facial scan data and the second 3D facial scan data.

In an embodiment, the first 3D facial scan data and the second 3D facial scan data may differ in at least one of a scanning device, a scanning time, a facial expression, a shape of a portion of a face and coordinate axes.

An example non-transitory computer-readable storage medium has stored thereon program instructions, which when executed by at least one hardware processor, performs extracting scan landmarks from 3D facial scan data using a convolutional neural network, extracting volume landmarks from 3D volumetric medical image data using the convolutional neural network and operating an initial registration of the 3D facial scan data and the 3D volumetric medical image data using the scan landmarks and the volume landmarks.

According to the automated registration method of the 3D facial scan data and the 3D volumetric medical image data using deep learning, the registration of the 3D facial scan data and the 3D volumetric medical image data may be fast and automatically operated utilizing the 3D facial scan data and the 3D volumetric medical image data itself without requiring a user input, an additional 3D model extraction process or a conversion of a data structure such as a voxelization.

In addition, the user input and the conversion of the data structure may not be required so that the accuracy of the registration may be enhanced.

In addition, the 3D facial scan data acquired with various facial expressions and at various times may be automatically matched to the 3D volumetric medical image data so that the registration result of the 3D facial scan data and the 3D volumetric medical image data may be used for maxillofacial analysis of a patient and an analysis of before/after surgery of the patient.

In addition, when the landmarks of the 3D facial scan data and the landmarks of the 3D volumetric medical image data are extracted using the same convolutional neural network, the network structure may be simplified and the computing load for extracting the landmarks may be reduced.

BRIEF DESCRIPTION OF THE DRAWINGS

The above and other features and advantages of the present inventive concept will become more apparent by describing in detailed embodiments thereof with reference to the accompanying drawings, in which.

DETAILED DESCRIPTION OF THE EMBODIMENTS

Figure 1:
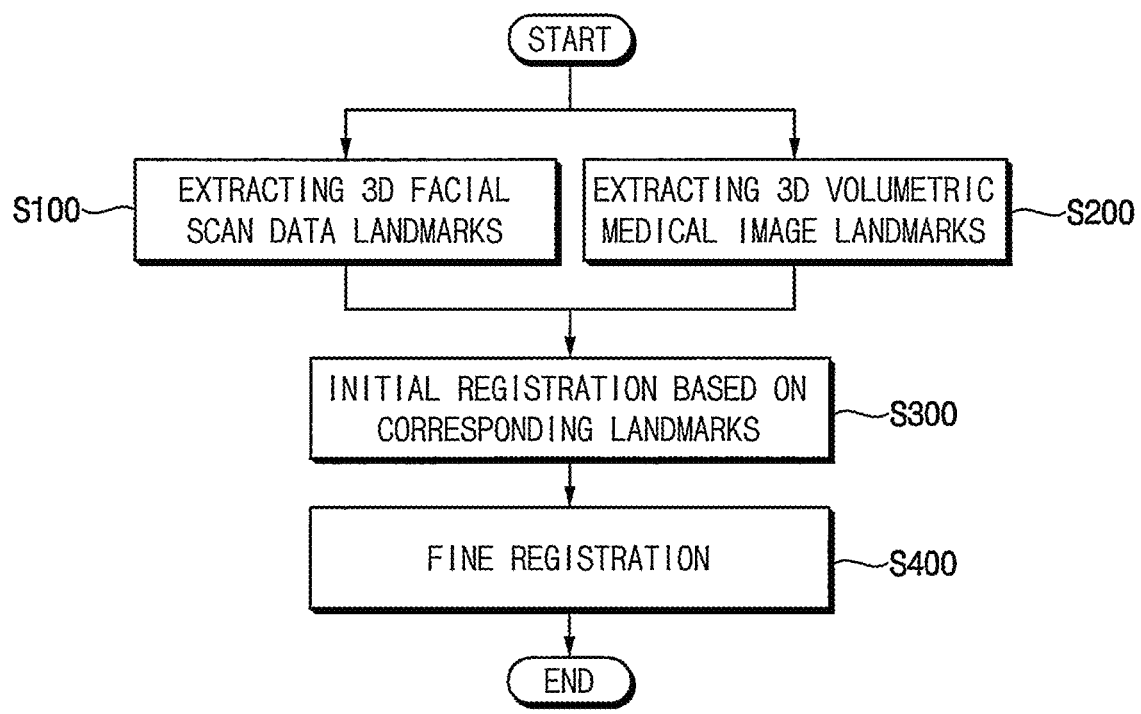
FIG. 1 is a flowchart diagram illustrating an automated registration method of 3D facial scan data and 3D volumetric medical image data using deep learning according to an embodiment of the present inventive concept.

The present inventive concept now will be described more fully hereinafter with reference to the accompanying drawings, in which embodiments of the present invention are shown. The present inventive concept may, however, be embodied in many different forms and should not be construed as limited to the embodiments set forth herein.

Rather, these embodiments are provided so that this disclosure will be thorough and complete, and will fully convey the scope of the present invention to those skilled in the art. Like reference numerals refer to like elements throughout.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the inventive concept as used herein.

Hereinafter, the present inventive concept will be explained in detail with reference to the accompanying drawings.

FIG. 1 is a flowchart diagram illustrating an automated registration method of 3D facial scan data and 3D volumetric medical image data using deep learning according to an embodiment of the present inventive concept.

Referring to FIG. 1, the automated registration method of the 3D facial scan data and the 3D volumetric medical image data includes extracting scan landmarks from the 3D facial scan data using a convolutional neural network (operation S100), extracting volume landmarks from the 3D volumetric medical image data using the convolutional neural network (operation S200) and operating an initial registration of the 3D facial scan data and the 3D volumetric medical image data using the scan landmarks and the volume landmarks (operation S300). The automated registration method may further include operating a fine registration (operation S400) after operating the initial registration (operation S300). In the fine registration (operation S400), a distance between a plurality of sampling points in the 3D facial scan data and a plurality of sampling points in the 3D volumetric medical scan data may be adjusted to be less than a threshold distance.

The 3D facial scan data may be mesh data including 3D vertexes and triangle or rectangles generated by connecting the 3D vertexes. The 3D facial scan data may be image data captured through a 3D scanner. Alternatively, the 3D facial scan data may be a 3D facial model generated by reconstructing 2D facial image or a 3D facial template model generated using landmarks of the 2D facial image. A filename extension of the 3D facial scan data is not limited, and may be, for example, one of ply, obj and stl.

The 3D volumetric medical image data may be a medical image in which a patient's anatomy is obtained as 3D volumetric image data. The 3D volumetric medical image data may be one of a computed tomography (CT) image, a cone-beam CT (CBCT) image, a magnetic resonance imaging (MRI) image and a positron emission tomography (PET) image. In the present embodiment, a case in which the 3D volumetric medical image data is the computed tomography (CT) image will be described as an example.

For example, the number of the scan landmarks extracted in the operation of extracting the scan landmarks (operation S100) may be equal to or greater than three. For example, the number of the volume landmarks extracted in the operation of extracting the volume landmarks (operation S200) may be equal to or greater than three. The three or more scan landmarks may correspond to the three or more volume landmarks.

The automated registration method of the 3D facial scan data and the 3D volumetric medical image data of the present invention may be operated by a computing apparatus.

Figure 2:
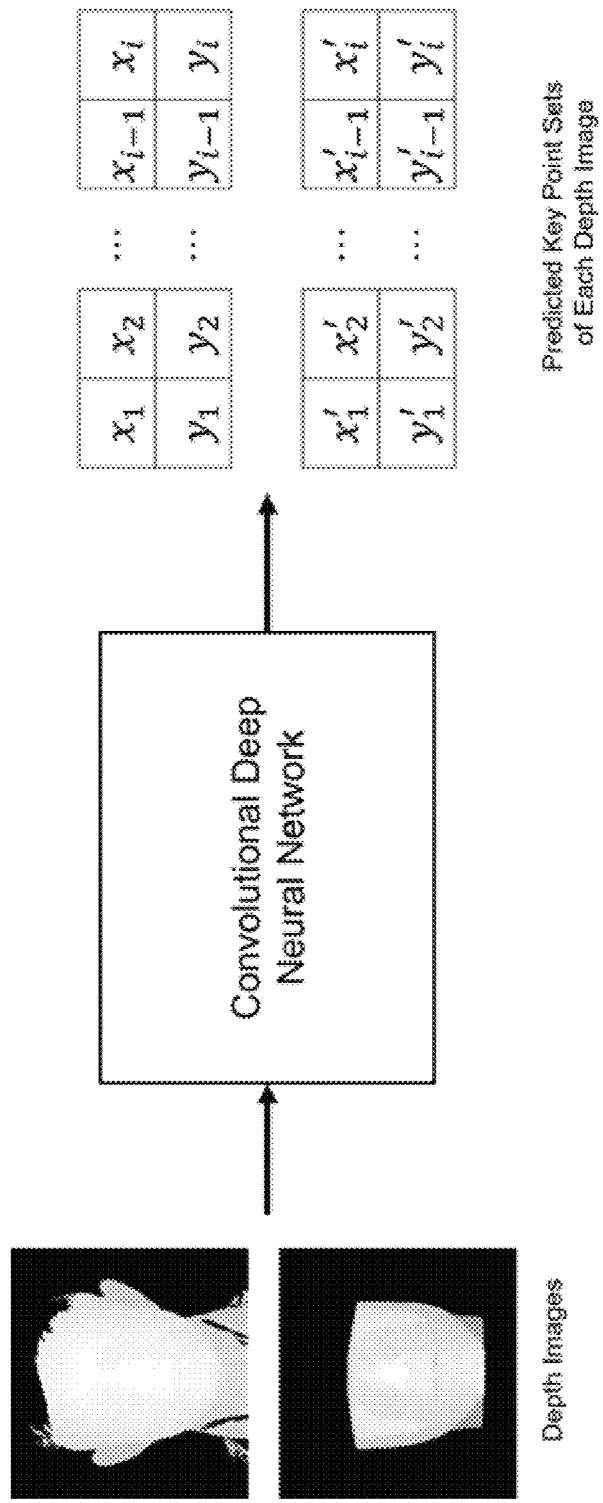
FIG. 2 is a diagram illustrating an example of an operation of extracting scan landmarks from the 3D facial scan data of FIG. 1 and an example of an operation of extracting volume landmarks from the 3D volumetric medical image of FIG. 1.
Figure 3:
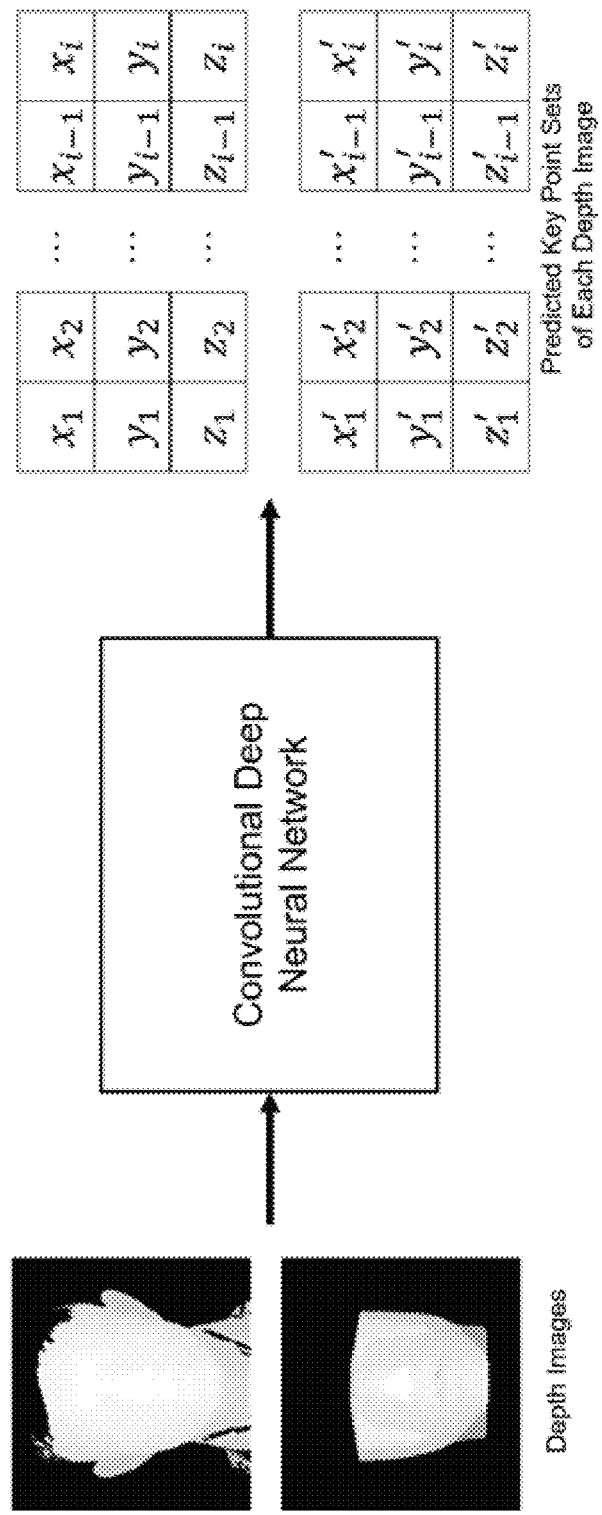
FIG. 3 is a diagram illustrating an example of the operation of extracting the scan landmarks from the 3D facial scan data of FIG. 1 and an example of the operation of extracting the volume landmarks from the 3D volumetric medical image of FIG. 1.
Figure 4:
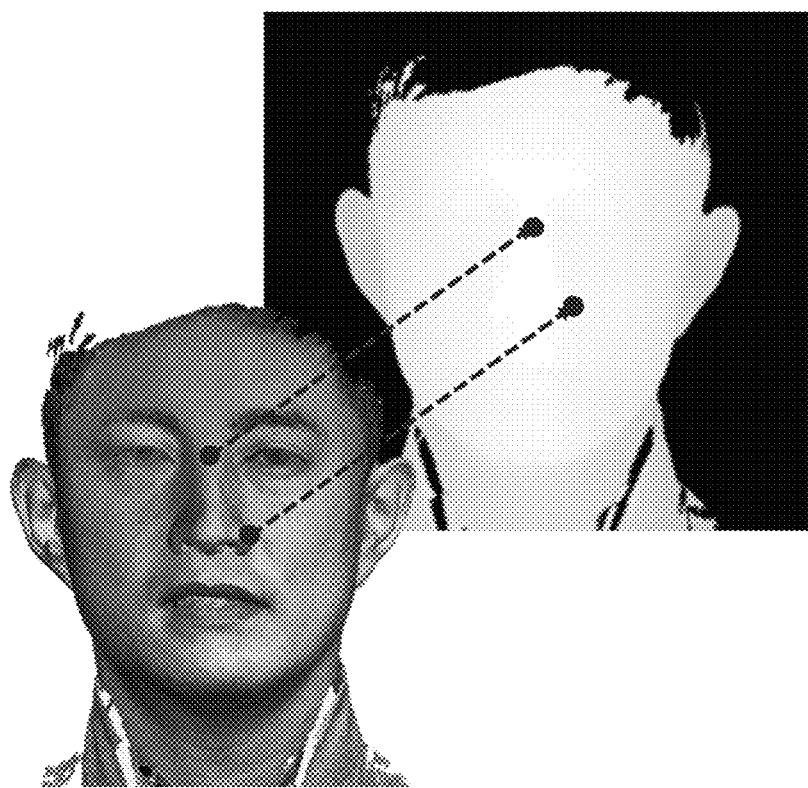
FIG. 4 is a diagram illustrating a method of generating a first 2D depth image from the 3D facial scan data.
Figure 5:
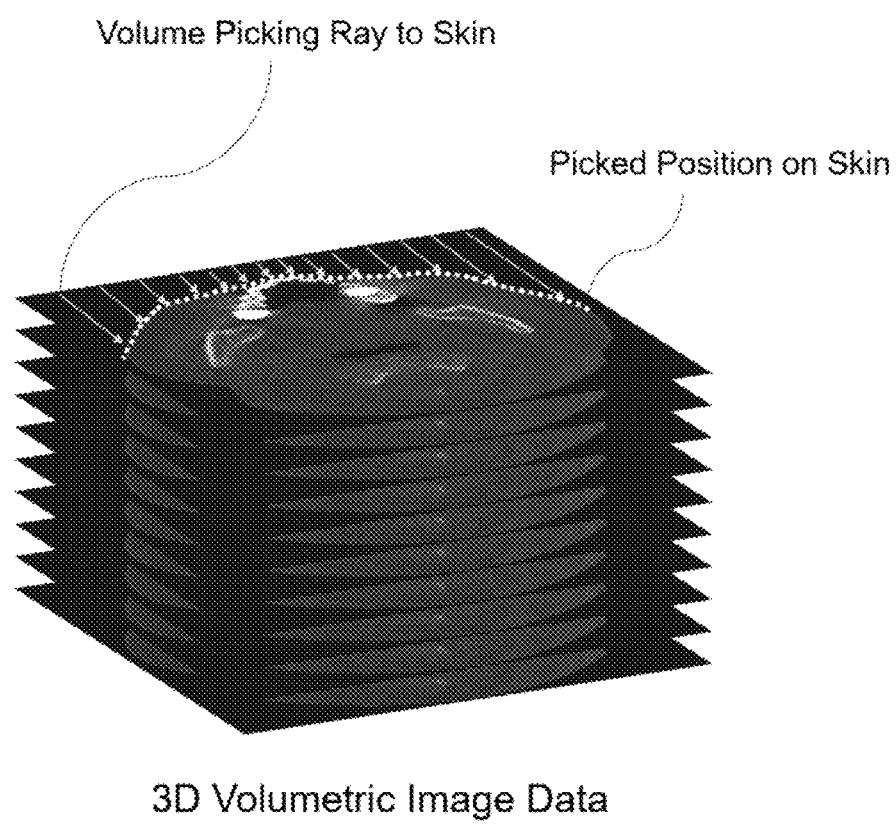
FIGS. 5 and 6 are diagrams illustrating a method of generating a second 2D depth image from the 3D volumetric medical image.
Figure 6:
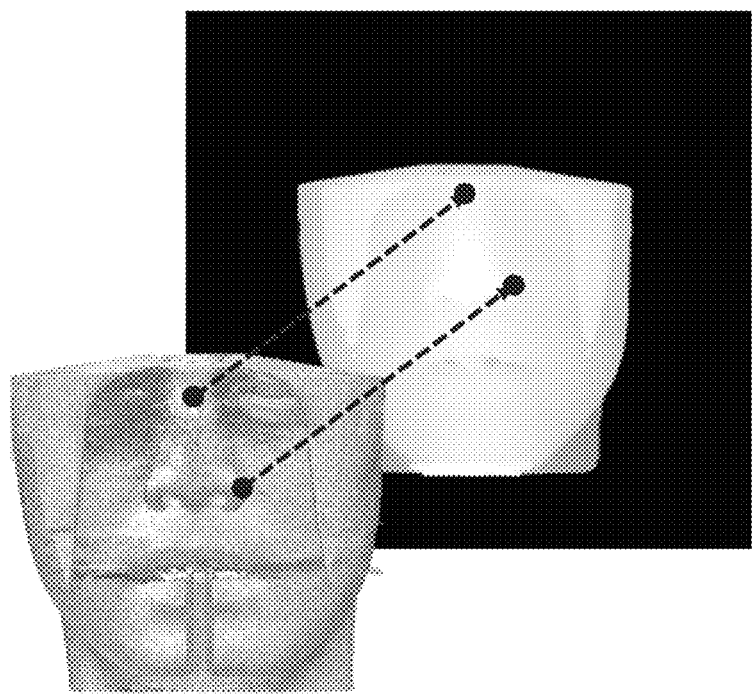

FIG. 2 is a diagram illustrating an example of an operation of extracting the scan landmarks from the 3D facial scan data of FIG. 1 and an example of an operation of extracting the volume landmarks from the 3D volumetric medical image of FIG. 1. FIG. 3 is a diagram illustrating an example of the operation of extracting the scan landmarks from the 3D facial scan data of FIG. 1 and an example of the operation of extracting the volume landmarks from the 3D volumetric medical image of FIG. 1. FIG. 4 is a diagram illustrating a method of generating a first 2D depth image from the 3D facial scan data. FIGS. 5 and 6 are diagrams illustrating a method of generating a second 2D depth image from the 3D volumetric medical image.

Referring to FIGS. 1 to 6, the operation of extracting the scan landmarks (operation S100) may include generating a first 2D depth image representing a distance between a first reference plane disposed outside the 3D facial scan data and a face surface in the 3D facial scan data. The first 2D depth image is illustrated in an upper left portion of FIG. 2.

FIG. 2 illustrates a case in which an input of the convolutional neural network is a 2D image and an output of the convolutional neural network is 2D coordinates.

For example, the input of the convolutional neural network may be the first 2D depth image. For example, the output of the convolutional neural network may be first 2D coordinates corresponding to the scan landmarks.

Herein, the operation of extracting the scan landmarks (operation S100) may further include inverse-projecting the first 2D coordinates to first 3D coordinates based on a transformation method used when generating the first 2D depth image. The first 3D coordinates may mean the landmarks of the 3D facial scan data.

Similarly, the operation of extracting the volume landmarks (operation S200) may include generating a second 2D depth image representing a distance between a second reference plane disposed outside the 3D volumetric medical image data and a face surface in the 3D volumetric medical image data. The second 2D depth image is illustrated in a lower left portion of FIG. 2.

For example, the input of the convolutional neural network may be the second 2D depth image. For example, the output of the convolutional neural network may be second 2D coordinates corresponding to the volume landmarks.

Herein, the operation of extracting the volume landmarks (operation S200) may further include inverse-projecting the second 2D coordinates to second 3D coordinates based on a transformation method used when generating the second 2D depth image. The second 3D coordinates may mean the landmarks of the 3D volumetric medical image data.

In FIG. 2, $x_i$, $y_i$ represents the first 2D coordinates of an i-th scan landmark extracted from the 3D facial scan data and $x'_i$, $y'_i$ represents the second 2D coordinates of an i-th volume landmark extracted from the 3D volumetric medical image data.

The scan landmark may be obtained by inverse-projecting the first 2D coordinates of FIG. 2 to the 3D facial scan data. The volume landmark may be obtained by inverse-projecting the second 2D coordinates of FIG. 2 to the 3D volumetric medical image data.

FIG. 3 illustrates a case in which an input of the convolutional neural network is a 2D image and an output of the convolutional neural network is 3D coordinates.

For example, the input of the convolutional neural network may be the first 2D depth image for the 3D facial scan data. For example, the output of the convolutional neural network may be first 3D coordinates corresponding to the scan landmarks.

In addition, the input of the convolutional neural network may be the second 2D depth image for the 3D volumetric medical image data. For example, the output of the convolutional neural network may be second 3D coordinates corresponding to the volume landmarks.

In FIG. 3, $x_i$, $y_i$, $z_i$ represents an i-th scan landmark extracted from the 3D facial scan data and $x'_i$, $y'_i$, $z'_i$ represents an i-th volume landmark extracted from the 3D volumetric medical image data.

In the present embodiment, the convolutional neural network for extracting the scan landmarks may be substantially the same as the convolutional neural network for extracting the volume landmarks. For example, the first 2D depth image of the 3D facial scan data and the second 2D depth image of the 3D volumetric medical image data may be inputted to the convolutional neural network. The first 2D coordinates or the first 3D coordinates corresponding to the scan landmarks and the second 2D coordinates or the second 3D coordinates corresponding to the volume landmarks may be outputted from the convolutional neural network.

Alternatively, the convolutional neural network for extracting the scan landmarks may be different from the convolutional neural network for extracting the volume landmarks. For example, the first 2D depth image of the 3D facial scan data may be inputted to a first convolutional neural network. The first 2D coordinates or the first 3D coordinates corresponding to the scan landmarks may be outputted from the first convolutional neural network. For example, the second 2D depth image of the 3D volumetric medical image data may be inputted to a second convolutional neural network which is different from the first convolutional neural network. The second 2D coordinates or the second 3D coordinates corresponding to the volume landmarks may be outputted from the second convolutional neural network.

FIG. 4 shows a process of generating a depth image form the 3D facial scan data. The depth image may be generated by representing a minimum distance from the surface of the 3D facial scan data to a virtual plane (the first reference plane) disposed at a certain distance from the 3D facial scan data as a brightness value (intensity). In FIG. 4, a lighter portion represents a shorter distance and a darker portion represents a longer distance. Alternatively, the brightness of the depth image may be inverted and represented in an opposite way.

FIGS. 5 and 6 show a process of obtaining a skin area from the 3D volumetric medical image data and generating a depth image using the obtained skin area. FIG. 5 shows a process of extracting a position of a skin surface where a brightness value (intensity) varies greatly when moving a virtual ray from a beginning to an end of the 3D volumetric medical image data and intersecting an air and the skin area into 3D coordinates. When a ray is irradiated at the beginning of the 3D volumetric medical image data, a first position where the brightness value changes greatly, and where the Hounsfield Unit (HU) value is between −100 and 300, which corresponds to skin and fat, may be considered as the skin area.

For example, in the operation of generating the second 2D depth image, while moving from a starting point of the 3D volumetric medical image data to an inside of the 3D volumetric medical image data, a position where a change in brightness value is greater than a threshold value firstly may be generated as a depth value of the second 2D depth image.

For example, in the operation of generating the second 2D depth image, while moving from a starting point of the 3D volumetric medical image data to an inside of the 3D volumetric medical image data, a position where a change in brightness value is greater than a threshold value firstly and having a brightness value within a predetermined range of skin brightness values may be generated as a depth value of the second 2D depth image. For example, the predetermined range of the skin brightness values may be Hounsfield Unit (HU) value between −100 and 300.

The depth image may be generated by representing a minimum distance from the 3D coordinates of the extracted skin surface to a virtual plane (the second reference plane) disposed at a certain distance from the 3D volumetric medical image data as a brightness value (intensity). In FIG. 6, a lighter portion represents a shorter distance and a darker portion represents a longer distance. Alternatively, the brightness of the depth image may be inverted and represented in an opposite way.

Figure 7:
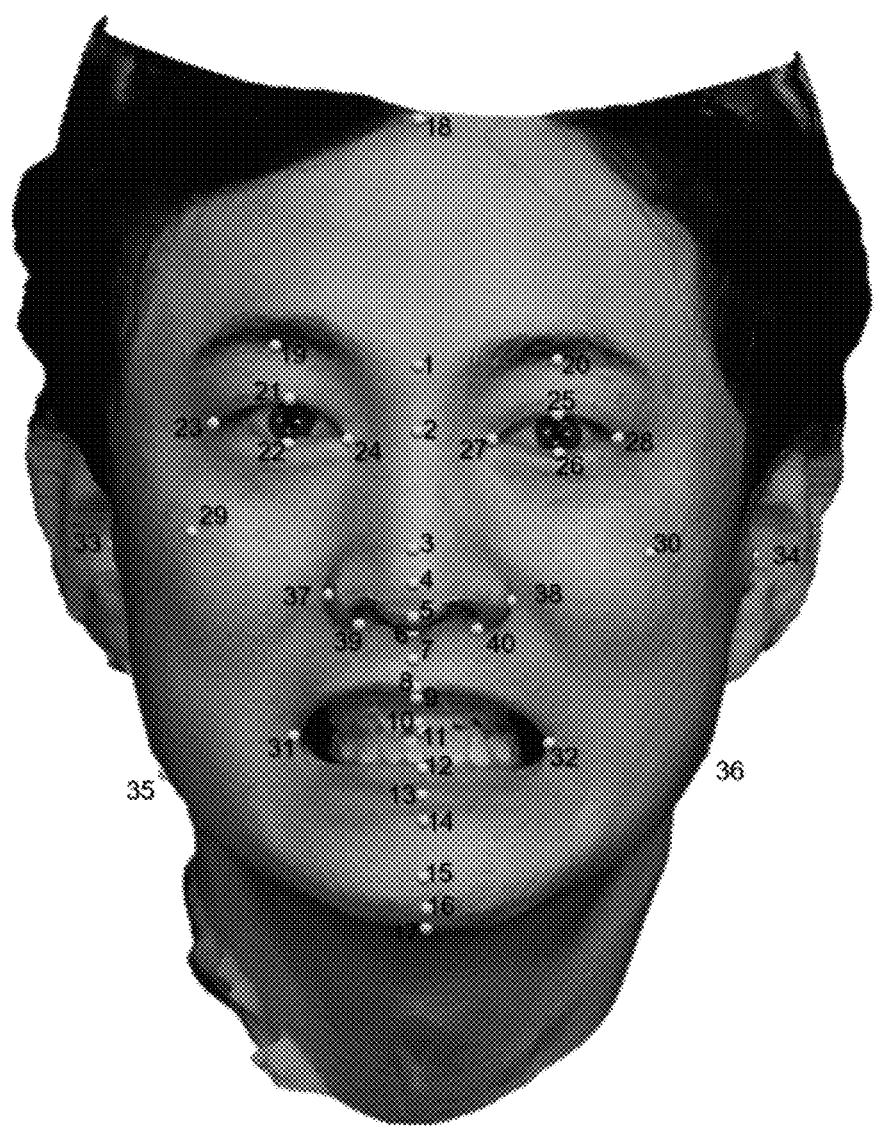
FIGS. 7 and 8 are diagrams illustrating examples of the scan landmarks and the volume landmarks.
Figure 8:
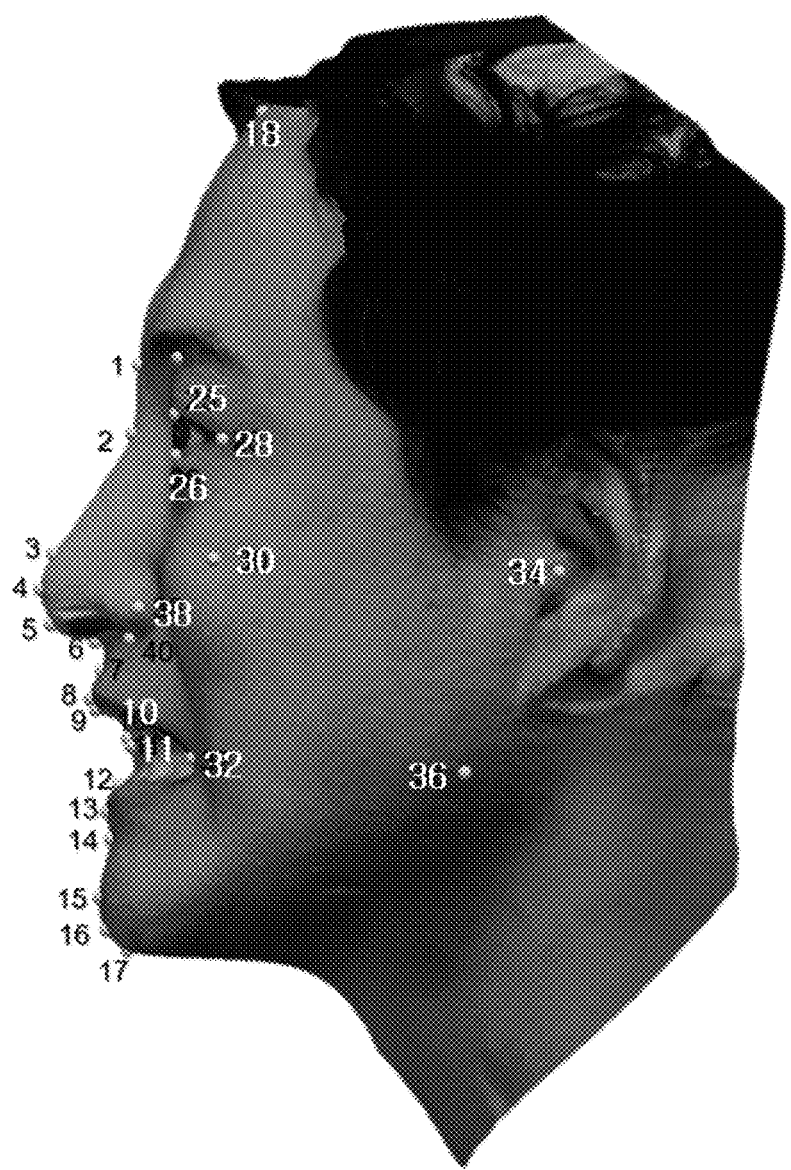

FIGS. 7 and 8 are diagrams illustrating examples of the scan landmarks and the volume landmarks.

Referring to FIGS. 1 to 8, the scan landmarks extracted in the operation (operation S100) of extracting the scan landmarks and the volume landmarks extracted in the operation (operation S200) of extracting the volume landmarks may include at least three among Soft tissue gabella (1), Soft tissue nasion (2), Supratip (3), Pronasale (4), Columella (5), Subnasale (6), Soft tissue A-point (7), Upper lip anterior point (8), Stomiom Superious (9), Lower point of gap between maxillary central incisors (10), Upper point of gap between mandibular central incisors (11), Stomiom Inferious (12), Lower lip anterior point (13), Soft tissue B-point (14), Soft tissue pogonion (15), Soft tissue gnathion (16), Soft tissue menton (17), Trichion (18), Right Orbitale superius (19), Left Orbitale superius (20), Right Palpebrale superius (21), Right Palpebrale inferious (22), Right Exocanthion (23), Right Endocanthion (24), Left Palpebrale superius (25), Left Palpebrale inferious (26), Left Endocanthion (27), Left Exocanthion (28), Right Zygion (29), Left Zygion (30), Right Cheilion (31), Left Cheilion (32), Right Tragus (33), Left Tragus (34), Right Soft tissue gonion (35), Left Soft tissue gonion (36), Right Alare (37), Left Alare (38), Right Alar curvature (39) and Left Alar curvature (40) respectively.

For example, the scan landmarks extracted in the operation (operation S100) of extracting the scan landmarks and the volume landmarks extracted in the operation (operation S200) of extracting the volume landmarks may include a skin surface landmark and an anterior tooth surface landmark.

Figure 9:
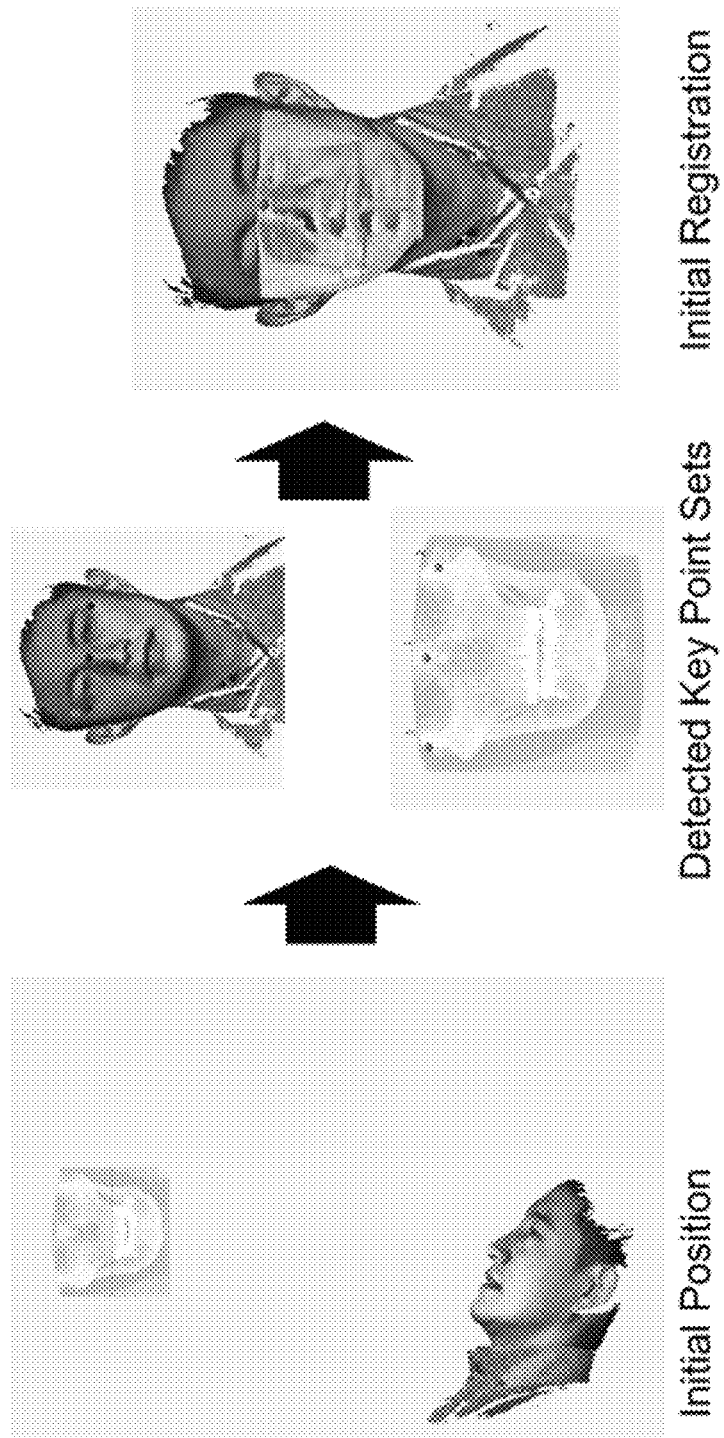
FIG. 9 is a diagram illustrating an initial registration of FIG. 1.
Figure 10:
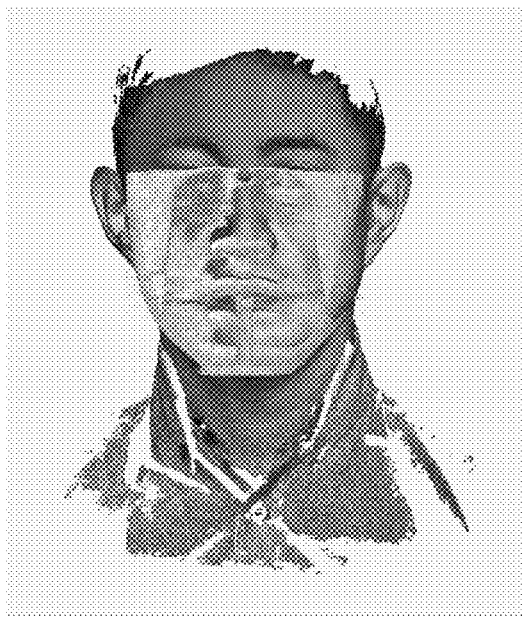
FIG. 10 is a diagram illustrating a fine registration of FIG. 1.
Figure 10:
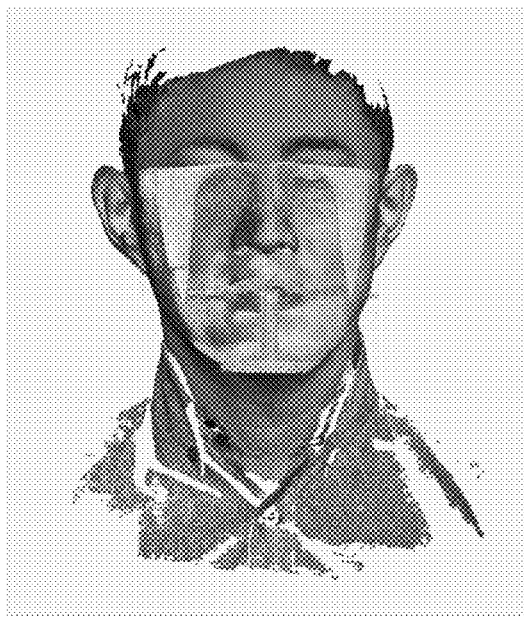
Figure 11:
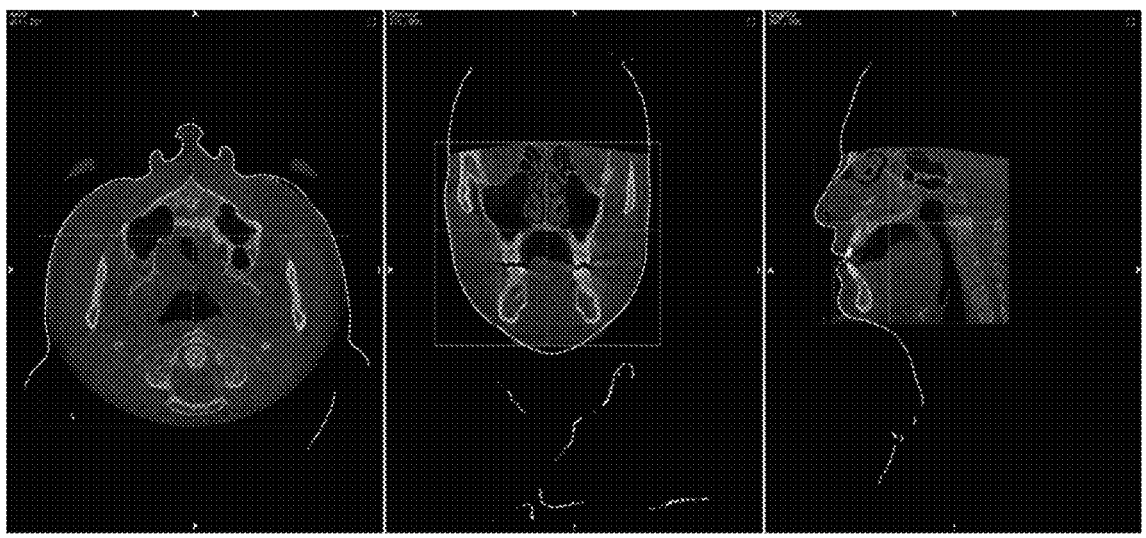
FIG. 11 is a diagram illustrating a result of the fine registration of FIG. 1.

FIG. 9 is a diagram illustrating an initial registration (operation S300) of FIG. 1. FIG. 10 is a diagram illustrating a fine registration (operation S400) of FIG. 1. FIG. 11 is a diagram illustrating a result of the fine registration (operation S400) of FIG. 1.

Referring to FIGS. 1 to 11, in the initial registration (operation S300) which is based on the corresponding landmarks, a transform matrix M may be calculated by a landmark transform using at least three pairs of the landmarks extracted in the operations S100 and S200. In the initial registration (operation S300), an error may be calculated by calculating a distance difference between corresponding landmarks.

The transform matrix M may minimize a distance difference between corresponding landmarks and may move the scan landmarks of the 3D facial scan data to a domain of the 3D volumetric medical image data. FIG. 9 shows a result of the initial registration (operation S300) using the corresponding landmarks.

For example, the scan landmarks extracted in the operation (operation S100) of extracting the scan landmarks and the volume landmarks extracted in the operation (operation S200) of extracting the volume landmarks may include Soft tissue nasion, Right Exocanthion and Left Exocanthion respectively.

For example, the registration of the 3D facial scan data and the 3D volumetric medical image data may be operated using Soft tissue nasion, Right Exocanthion and Left Exocanthion in FIG. 10.

In the fine registration (operation S400), a precise registration may be performed to further match the 3D volumetric medical image and the 3D facial scan data after the initial registration (operation S300). FIGS. 10 and 11 show a result of the fine registration (operation S400).

As shown in FIG. 10, the 3D volumetric medical image data and the 3D facial scan data may be well matched in the result of the fine registration (operation S400) more than in the result of the initial registration (operation S300).

FIG. 11 visualizes the result of the fine registration (operation S400) as multi-view slide images of the 3D volumetric medical image data. The outer solid line in FIG. 11 corresponds to the skin surface of the 3D facial scan data. In FIG. 11, the outer solid line representing the skin surface of the 3D facial scan data is precisely matched to the 3D volumetric medical image data.

According to the present embodiment, the registration of the 3D facial scan data and the 3D volumetric medical image data may be fast and automatically operated utilizing the 3D facial scan data and the 3D volumetric medical image data itself without requiring a user input, an additional 3D model extraction process or a conversion of a data structure such as a voxelization.

In addition, the user input and the conversion of the data structure may not be required so that the accuracy of the registration may be enhanced.

In addition, when the landmarks of the 3D facial scan data and the landmarks of the 3D volumetric medical image data are extracted using the same convolutional neural network, the network structure may be simplified and the computing load for extracting the landmarks may be reduced.

Figure 12:
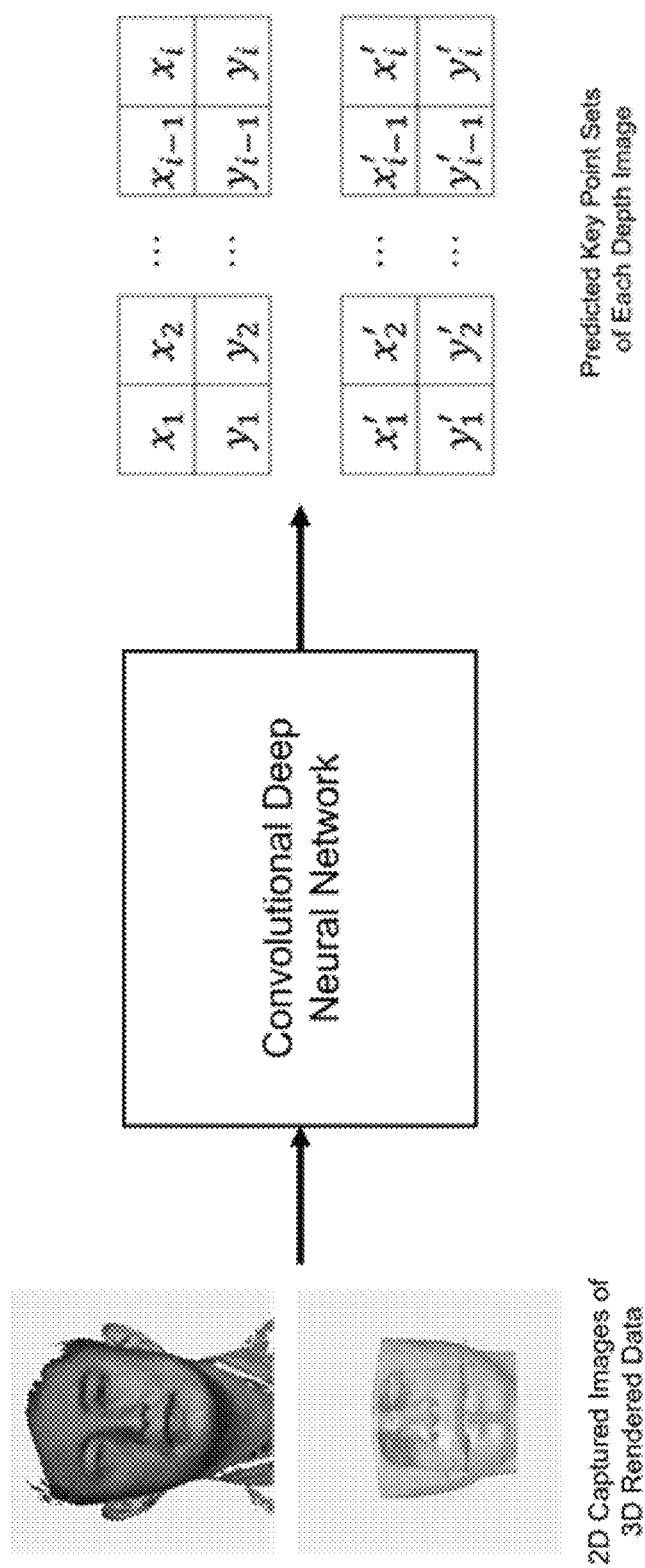
FIG. 12 is a diagram illustrating an example of an operation of extracting scan landmarks from the 3D facial scan data of FIG. 1 and an example of an operation of extracting volume landmarks from the 3D volumetric medical image of FIG. 1.
Figure 13:
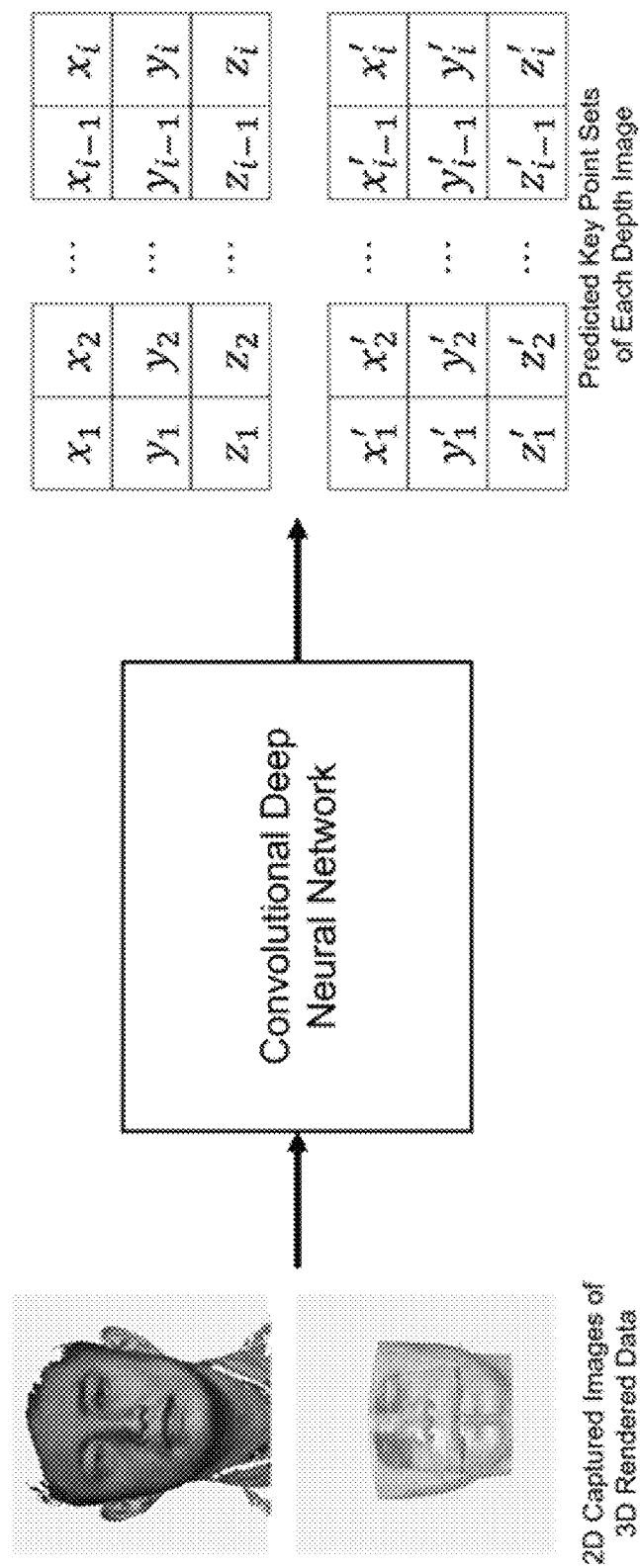
FIG. 13 is a diagram illustrating an example of an operation of extracting scan landmarks from the 3D facial scan data of FIG. 1 and an example of an operation of extracting volume landmarks from the 3D volumetric medical image of FIG. 1.
Figure 14:
FIG. 14 is a diagram illustrating a first captured image generated by capturing the 3D facial scan data.
Figure 15:
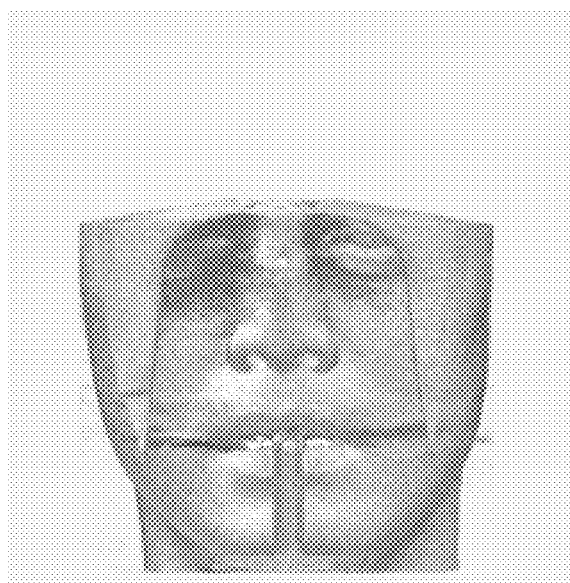
FIG. 15 is a diagram illustrating a second captured image generated by capturing the 3D volumetric medical image data.

FIG. 12 is a diagram illustrating an example of an operation of extracting scan landmarks from the 3D facial scan data of FIG. 1 and an example of an operation of extracting volume landmarks from the 3D volumetric medical image of FIG. 1. FIG. 13 is a diagram illustrating an example of an operation of extracting scan landmarks from the 3D facial scan data of FIG. 1 and an example of an operation of extracting volume landmarks from the 3D volumetric medical image of FIG. 1. FIG. 14 is a diagram illustrating a first captured image generated by capturing the 3D facial scan data. FIG. 15 is a diagram illustrating a second captured image generated by capturing the 3D volumetric medical image data.

The automated registration method according to the present embodiment is substantially the same as the automated registration method of the previous embodiment explained referring to FIGS. 1 to 11 except for the input of the convolutional neural network. Thus, the same reference numerals will be used to refer to the same or like parts as those described in the previous embodiment of FIGS. 1 to 11 and any repetitive explanation concerning the above elements will be omitted.

Referring to FIGS. 1 and 7 to 15, the automated registration method of the 3D facial scan data and the 3D volumetric medical image data includes extracting scan landmarks from the 3D facial scan data using a convolutional neural network (operation S100), extracting volume landmarks from the 3D volumetric medical image data using the convolutional neural network (operation S200) and operating an initial registration of the 3D facial scan data and the 3D volumetric medical image data using the scan landmarks and the volume landmarks (operation S300). The automated registration method may further include operating a fine registration (operation S400) after operating the initial registration (operation S300). In the fine registration (operation S400), a distance between a plurality of sampling points in the 3D facial scan data and a plurality of sampling points in the 3D volumetric medical scan data may be adjusted to be less than a threshold distance.

In the operation of extracting the scan landmarks (operation S100), a first 2D captured image may be generated by capturing the 3D facial scan data. The first 2D captured image is illustrated in an upper left portion of FIG. 12 and FIG. 14.

FIG. 12 illustrates a case in which an input of the convolutional neural network is a 2D image and an output of the convolutional neural network is 2D coordinates.

For example, the input of the convolutional neural network may be the first 2D captured image. For example, the output of the convolutional neural network may be first 2D coordinates corresponding to the scan landmarks.

Herein, the operation of extracting the scan landmarks (operation S100) may further include inverse-projecting the first 2D coordinates to first 3D coordinates. The first 3D coordinates may mean the landmarks of the 3D facial scan data.

Similarly, in the operation of extracting the volume landmarks (operation S200), a second 2D captured image may be generated by capturing the 3D volumetric medical image data. The second 2D captured image is illustrated in a lower left portion of FIG. 12 and FIG. 15.

For example, the input of the convolutional neural network may be the second 2D captured image. For example, the output of the convolutional neural network may be second 2D coordinates corresponding to the volume landmarks.

Herein, the operation of extracting the volume landmarks (operation S200) may further include inverse-projecting the second 2D coordinates to second 3D coordinates. The second 3D coordinates may mean the landmarks of the 3D volumetric medical image data.

FIG. 13 illustrates a case in which an input of the convolutional neural network is a 2D image and an output of the convolutional neural network is 3D coordinates.

For example, the input of the convolutional neural network may be the first 2D captured image for the 3D facial scan data. For example, the output of the convolutional neural network may be first 3D coordinates corresponding to the scan landmarks.

In addition, the input of the convolutional neural network may be the second 2D captured image for the 3D volumetric medical image data. For example, the output of the convolutional neural network may be second 3D coordinates corresponding to the volume landmarks.

According to the present embodiment, the registration of the 3D facial scan data and the 3D volumetric medical image data may be fast and automatically operated utilizing the 3D facial scan data and the 3D volumetric medical image data itself without requiring a user input, an additional 3D model extraction process or a conversion of a data structure such as a voxelization.

In addition, the user input and the conversion of the data structure may not be required so that the accuracy of the registration may be enhanced.

In addition, when the landmarks of the 3D facial scan data and the landmarks of the 3D volumetric medical image data are extracted using the same convolutional neural network, the network structure may be simplified and the computing load for extracting the landmarks may be reduced.

Figure 16:
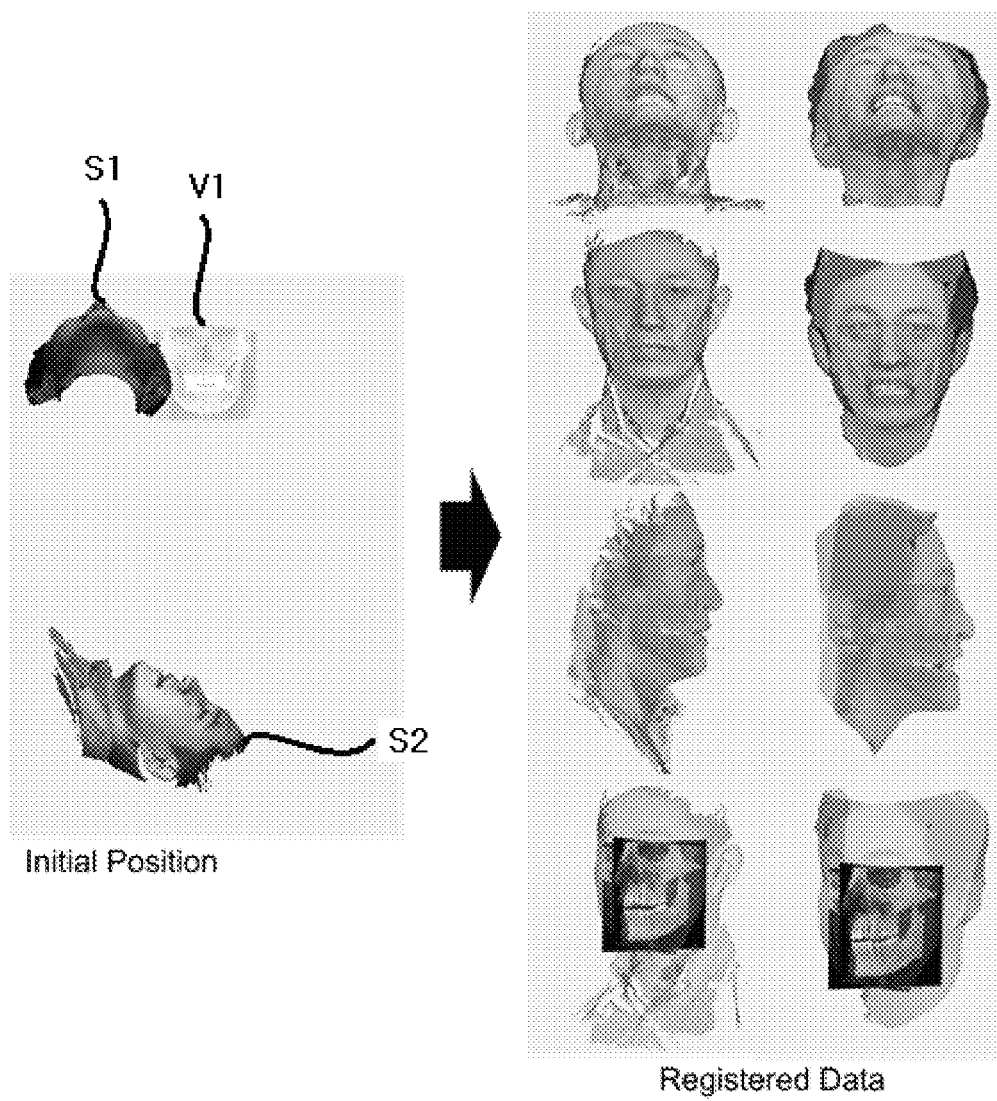
FIG. 16 is a diagram illustrating an example of an automated registration of first 3D facial scan data, second 3D facial scan data and 3D volumetric medical image data.
Figure 17:
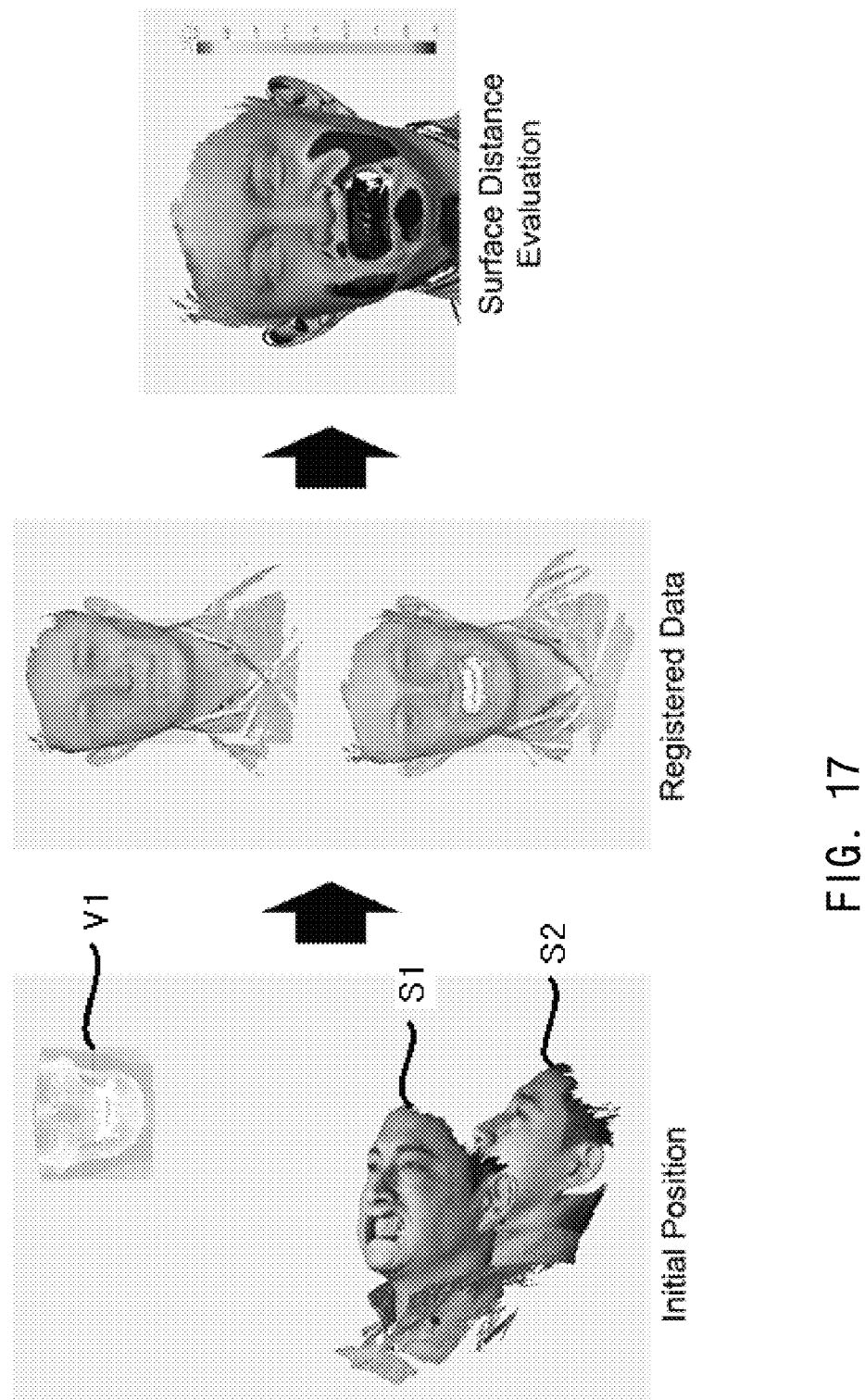
FIG. 17 is a diagram illustrating an example of an automated registration of first 3D facial scan data, second 3D facial scan data and 3D volumetric medical image data.

FIG. 16 is a diagram illustrating an example of an automated registration of first 3D facial scan data S1, second 3D facial scan data S2 and 3D volumetric medical image data V1. FIG. 17 is a diagram illustrating an example of an automated registration of first 3D facial scan data S1, second 3D facial scan data S2 and 3D volumetric medical image data V1.

The automated registration method according to the present embodiment is substantially the same as the automated registration method of the previous embodiment explained referring to FIGS. 1 to 11 except that two 3D facial scan data are matched to one 3D volumetric medical image data. Thus, the same reference numerals will be used to refer to the same or like parts as those described in the previous embodiment of FIGS. 1 to 11 and any repetitive explanation concerning the above elements will be omitted.

Referring to FIGS. 1 to 17, the automated registration method of the 3D facial scan data and the 3D volumetric medical image data includes extracting first scan landmarks from first 3D facial scan data S1 using a convolutional neural network, extracting second scan landmarks from second 3D facial scan data S2 using the convolutional neural network, extracting volume landmarks from the 3D volumetric medical image data V1 using the convolutional neural network, operating an initial registration of the first 3D facial scan data S1, the second 3D facial scan data S2 and the 3D volumetric medical image data V1 using the first scan landmarks, the second scan landmarks and the volume landmarks and calculating a surface distance between the first 3D facial scan data S1 and the second 3D facial scan data S2.

For example, the first scan landmarks, the second scan landmarks and the volume landmarks may be extracted from the same convolutional neural network.

Alternatively, the first scan landmarks and the second scan landmarks may be extracted from a first convolutional neural network and the volume landmarks may be extracted from a second convolutional neural network.

For example, the first 3D facial scan data S1 and the second 3D facial scan data S2 may differ in at least one of a scanning device, a scanning time, a facial expression, a shape of a specific portion of the face and coordinate axes.

FIG. 16 illustrates a case in which two 3D facial scan data S1 and S2 of the same patient with different scanning devices, different facial expressions and different coordinate axes are matched to one 3D volumetric medical image data V1.

FIG. 17 illustrates a case in which two 3D facial scan data S1 and S2 of the same patient with the same scanning device, but with different facial expressions and different coordinate axes are matched to one 3D volumetric medical image data V1.

FIG. 17 illustrates an analysis of a surface distance difference by calculating the surface distance between the first 3D facial scan data S1 and the second 3D facial scan data S2.

As shown in FIGS. 16 and 17, the 3D facial scan data S1 and S2 having different coordinate axes are matched to the same 3D volumetric medical image data V1 and the coordinate axes of the 3D facial scan data S1 and S2 coincide with each other so that the first 3D facial scan data S1 and the second 3D facial scan data S2 may be compared and analyzed.

In FIG. 16, two 3D facial scan data of the same patient with different scanning devices, different scanning times and different facial expressions are matched to one 3D volumetric medical image data so that the two 3D facial scan data may be compared and analyzed in various angles. In FIG. 17, two 3D facial scan data of the same patient with different facial expressions are matched to one 3D volumetric medical image data so that a face change area may be analyzed.

The 3D volumetric medical image data is expensive to acquire, and in the case of CT or CBCT, it is difficult to acquire multiple times due to the risk of radiation exposure. Therefore, it is difficult to compare the 3D volumetric medical image data before surgery and the 3D volumetric medical image data after surgery and it is difficult to use the 3D volumetric medical image data for procedures and surgical simulations in various facial expression states. In the present embodiment, the 3D facial scan data acquired with various facial expressions and at various times may be automatically matched to the 3D volumetric medical image data so that the registration result of the 3D facial scan data and the 3D volumetric medical image data may be used for maxillofacial analysis of a patient and an analysis of before/after surgery of the patient.

According to the present embodiment, the registration of the 3D facial scan data and the 3D volumetric medical image data may be fast and automatically operated utilizing the 3D facial scan data and the 3D volumetric medical image data itself without requiring a user input, an additional 3D model extraction process or a conversion of a data structure such as a voxelization.

In addition, the user input and the conversion of the data structure may not be required so that the accuracy of the registration may be enhanced.

In addition, when the landmarks of the 3D facial scan data and the landmarks of the 3D volumetric medical image data are extracted using the same convolutional neural network, the network structure may be simplified and the computing load for extracting the landmarks may be reduced.

According to an embodiment of the present inventive concept, a non-transitory computer-readable storage medium having stored thereon program instructions of the automated registration method of 3D facial scan data and 3D volumetric medical image data may be provided. The above mentioned method may be written as a program executed on the computer. The method may be implemented in a general purpose digital computer which operates the program using a computer-readable medium. In addition, the structure of the data used in the above mentioned method may be written on a computer readable medium through various means. The computer readable medium may include program instructions, data files and data structures alone or in combination. The program instructions written on the medium may be specially designed and configured for the present inventive concept, or may be generally known to a person skilled in the computer software field. For example, the computer readable medium may include a magnetic medium such as a hard disk, a floppy disk and a magnetic tape, an optical recording medium such as CD-ROM and DVD, a magneto-optical medium such as floptic disc and a hardware device specially configured to store and execute the program instructions such as ROM, RAM and a flash memory. For example, the program instructions may include a machine language codes produced by a compiler and high-level language codes which may be executed by a computer using an interpreter or the like. The hardware device may be configured to operate as one or more software modules to perform the operations of the present inventive concept.

In addition, the above mentioned automated registration method of 3D facial scan data and 3D volumetric medical image data may be implemented in a form of a computer-executed computer program or an application which are stored in a storage method.

The present inventive concept is related to the automated registration method of 3D facial scan data and 3D volumetric medical image data and the non-transitory computer-readable storage medium having stored thereon program instructions of the automated registration method of 3D facial scan data and 3D volumetric medical image data. According to the present inventive concept, the time and the effort for the automated registration. In addition, the 3D facial scan data acquired with various facial expressions and at various times may be automatically matched to the 3D volumetric medical image data so that the registration result of the 3D facial scan data and the 3D volumetric medical image data may be used for maxillofacial analysis of a patient and an analysis of before/after surgery of the patient.

The foregoing is illustrative of the present inventive concept and is not to be construed as limiting thereof. Although a few embodiments of the present inventive concept have been described, those skilled in the art will readily appreciate that many modifications are possible in the embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of the present inventive concept and is not to be construed as limited to the specific embodiments disclosed, and that modifications to the disclosed embodiments, as well as other embodiments, are intended to be included within the scope of the appended claims. The present inventive concept is defined by the following claims, with equivalents of the claims to be included therein.

What is claimed is:

1. An automated registration method of 3D facial scan data and 3D volumetric medical image data using deep learning, the method comprising:

obtaining 3D facial scan data and 3D volumetric medical image data from respective imaging devices;

generating two-dimensional (2D) depth images from the 3D facial scan data and the 3D volumetric medical image data;

extracting scan landmarks from both 2D depth images and the 3D facial scan data, using a convolutional neural network;

extracting volume landmarks from both 2D depth images and the 3D volumetric medical image data using the convolutional neural network;

wherein the convolutional neural network processes the data without requiring manual segmentation;

operating an initial registration of the 3D facial scan data and the 3D volumetric medical image data by automatically aligning the scan landmarks and the volume landmarks; and refining the alignment by adapting sampling points between the 3D facial scan data and the 3D volumetric medical image data to achieve sub-threshold distances.

2. The method of claim 1, wherein the extracting scan landmarks comprises:

generating a first 2D depth image representing a distance between a first reference plane disposed outside the 3D facial scan data and a face surface in the 3D facial scan data.

3. The method of claim 2, wherein an input of the convolutional neural network is the first 2D depth image, and wherein an output of the convolutional neural network is first 2D coordinates corresponding to the scan landmarks.

4. The method of claim 3, wherein the extracting scan landmarks further comprises:

inverse-projecting the first 2D coordinates to first 3D coordinates based on a transformation method used when generating the first 2D depth image.

5. The method of claim 2, wherein an input of the convolutional neural network is the first 2D depth image, and wherein an output of the convolutional neural network is first 3D coordinates corresponding to the scan landmarks.

6. The method of claim 1, wherein the extracting volume landmarks comprises:

generating a second 2D depth image representing a distance between a second reference plane disposed outside the 3D volumetric medical image data and a face surface in the 3D volumetric medical image data.

7. The method of claim 6, wherein, in the generating a second 2D depth image, while moving from a starting point of the 3D volumetric medical image data to an inside of the 3D volumetric medical image data, a position where a change in brightness value is greater than a threshold value firstly is generated as a depth value of the second 2D depth image.

8. The method of claim 6, wherein, in the generating a second 2D depth image, while moving from a starting point of the 3D volumetric medical image data to an inside of the 3D volumetric medical image data, a position where a change in brightness value is greater than a threshold value firstly and having a brightness value within a predetermined range of skin brightness values is generated as a depth value of the second 2D depth image.

9. The method of claim 6, wherein an input of the convolutional neural network is the second 2D depth image, and
wherein an output of the convolutional neural network is second 2D coordinates corresponding to the volume landmarks.

10. The method of claim 9, wherein the extracting volume landmarks further comprises:
inverse-projecting the second 2D coordinates to second 3D coordinates based on a transformation method used when generating the second 2D depth image.

11. The method of claim 6, wherein an input of the convolutional neural network is the second 2D depth image, and
wherein an output of the convolutional neural network is second 3D coordinates corresponding to the scan landmarks.

12. The method of claim 1, wherein the extracting scan landmarks comprises:
generating a first 2D captured image by capturing the 3D facial scan data.

13. The method of claim 12, wherein an input of the convolutional neural network is the first 2D captured image, and
wherein an output of the convolutional neural network is first 3D coordinates corresponding to the scan landmarks.

14. The method of claim 12, wherein the extracting volume landmarks comprises:
generating a second 2D captured image by capturing the 3D volume medical image data.

15. The method of claim 14, wherein an input of the convolutional neural network is the second 2D captured image, and
wherein an output of the convolutional neural network is second 3D coordinates corresponding to the volume landmarks.

16. The method of claim 1, wherein a number of the scan landmarks extracted in the extracting scan landmarks is equal to or greater than three,
wherein a number of the volume landmarks extracted in the extracting volume landmarks is equal to or greater than three, and
wherein the three or more scan landmarks correspond to the three or more volume landmarks.

17. The method of claim 16, wherein the scan landmarks extracted in the extracting scan landmarks and the volume landmarks extracted in the extracting volume landmarks include Soft tissue nasion, Right Exocanthion and Left Exocanthion respectively.

18. The method of claim 1, wherein the scan landmarks extracted in the extracting scan landmarks and the volume landmarks extracted in the extracting volume landmarks include at least three among Soft tissue gabella, Soft tissue nasion, Supratip, Pronasale, Columella, Subnasale, Soft tissue A-point, Upper lip anterior point, Stomiom Superious, Lower point of gap between maxillary central incisors, Upper point of gap between mandibular central incisors, Stomiom Inferious, Lower lip anterior point, Soft tissue B-point, Soft tissue pogonion, Soft tissue gnathion, Soft tissue menton, Trichion, Right Orbitale superius, Left Orbitale superius, Right Palpebrale superius, Right Palpebrale inferious, Right Exocanthion, Right Endocanthion, Left Palpebrale superius, Left Palpebrale inferious, Left Endocanthion, Left Exocanthion, Right Zygion, Left Zygion, Right Cheilion, Left Cheilion, Right Tragus, Left Tragus, Right Soft tissue gonion, Left Soft tissue gonion, Right Alare, Left Alare, Right Alar curvature and Left Alar curvature respectively.

19. The method of claim 1, wherein the 3D facial scan data are mesh data including 3D vertexes and triangle or rectangles generated by connecting the 3D vertexes.

20. The method of claim 1, wherein the 3D volumetric medical image data are a medical image in which a patient's anatomy is obtained as 3D volumetric image data, and
wherein the 3D volumetric medical image data are one of a computed tomography (CT) image, a cone-beam CT (CBCT) image, a magnetic resonance imaging (MRI) image and a positron emission tomography (PET) image.

21. The method of claim 1, further comprising:
operating a fine registration after the operating an initial registration,
wherein in the fine registration, a distance between a plurality of sampling points in the 3D facial scan data and a plurality of sampling points in the 3D volumetric medical scan data is adjusted to be less than a threshold distance.

22. A non-transitory computer-readable storage medium having stored thereon program instructions, which when executed by at least one hardware processor, performs the method of claim 1.

23. An automated registration method of 3D facial scan data and 3D volumetric medical image data using deep learning, the method comprising:
obtaining 3D facial scan data and 3D volumetric medical image data from respective imaging devices;
generating two-dimensional (2D) depth images from the 3D facial scan data and the 3D volumetric medical image data;
extracting scan landmarks from both 2D depth images and the 3D facial scan data, using a first convolutional neural network;
extracting volume landmarks from both 2D depth images and the 3D volumetric medical image data using a second convolutional neural network different from the first convolutional neural network;
wherein the first and second convolutional neural network process the data without requiring manual segmentation;
operating an initial registration of the 3D facial scan data and the 3D volumetric medical image data by automatically aligning the scan landmarks and the volume landmarks; and
refining the alignment by adapting sampling points between the 3D facial scan data and the 3D volumetric medical image data to achieve sub-threshold distances.

24. An automated registration method of 3D facial scan data and 3D volumetric medical image data using deep learning, the method comprising:
obtaining 3D facial scan data and 3D volumetric medical image data from respective imaging devices;

generating two-dimensional (2D) depth images from the 3D facial scan data and the 3D volumetric medical image data;

extracting scan landmarks from both 2D depth images and the 3D facial scan data, using a convolutional neural network;

extracting volume landmarks from both 2D depth images and the 3D volumetric medical image data using the convolutional neural network;

wherein the convolutional neural network processes the data without requiring manual segmentation;

calculating a surface distance between the first 3D facial scan data and the second 3D facial scan data;

operating an initial registration of the 3D facial scan data and the 3D volumetric medical image data using the scan landmarks and the volume landmarks by automatically aligning the scan landmarks and the volume landmarks; and refining the alignment by adapting sampling points between the 3D facial scan data and the 3D volumetric medical image data to achieve sub-threshold distances.

25. The method of claim 24, wherein the first 3D facial scan data and the second 3D facial scan data differ in at least one of a scanning device, a scanning time, a facial expression, a shape of a portion of a face and coordinate axes.

* * * * *